US010675559B2

(12) United States Patent
Leinekugel Le Cocq et al.

(10) Patent No.: US 10,675,559 B2
(45) Date of Patent: Jun. 9, 2020

(54) SIMULATED MOVING BED SEPARATION METHOD AND DEVICE WITH BYPASS FLUID FLOW

(71) Applicant: IFP Energies nouvelles, Rueil-Malmaison (FR)

(72) Inventors: Damien Leinekugel Le Cocq, Rueil-Malmaison (FR); Gerard Hotier, Rueil-Malmaison (FR); Pierre-Yves Le Goff, Rueil-Malmaison (FR); Fabian Lambert, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/441,547

(22) Filed: Jun. 14, 2019

(65) Prior Publication Data
US 2019/0388801 A1    Dec. 26, 2019

(30) Foreign Application Priority Data

Jun. 20, 2018    (FR) .................................... 18/55.449

(51) Int. Cl.
*B01D 15/18*    (2006.01)
*C07C 7/00*    (2006.01)
*C07C 7/13*    (2006.01)

(52) U.S. Cl.
CPC ....... *B01D 15/1835* (2013.01); *B01D 15/185* (2013.01); *C07C 7/005* (2013.01); *C07C 7/13* (2013.01); *B01D 2215/026* (2013.01)

(58) Field of Classification Search
CPC .............. B01D 15/1835; B01D 15/185; B01D 2215/02; C07C 7/13; C07C 7/12
USPC ......................... 585/820, 822, 826, 827, 828
See application file for complete search history.

(56) References Cited

U.S. PATENT DOCUMENTS

2010/0048973 A1*   2/2010  Decoodt ............ B01D 15/1835
                                                    585/822

* cited by examiner

*Primary Examiner* — Thuan D Dang
(74) *Attorney, Agent, or Firm* — Millen White Zelano and Branigan, PC; Csaba Henter

(57) ABSTRACT

Method for the simulated moving bed separation of a feedstock (F), in which when a fluid/effluent (feedstock F, desorbent D, extract E, raffinate R) is injected/withdrawn into/from a chosen plate ($P_i$) using an external bypass line ($L_{i-1/i}$, $L_{i/i+1}$) connected to said chosen plate ($P_i$), the flow rate within the said external bypass line ($L_{i-1/i}$, $L_{i/i+1}$) is controlled in such a way that: a major proportion of the fluid/effluent (F, D, E, R) is injected/withdrawn into/from the chosen plate ($P_i$); and a minor proportion of the fluid/effluent (F, D, E, R) is injected/withdrawn into/from the adjacent plate ($P_{i-1}$, $P_{i+1}$) connected to the said external bypass line ($L_{i-1/i}$, $L_{i/i+1}$).

9 Claims, 1 Drawing Sheet

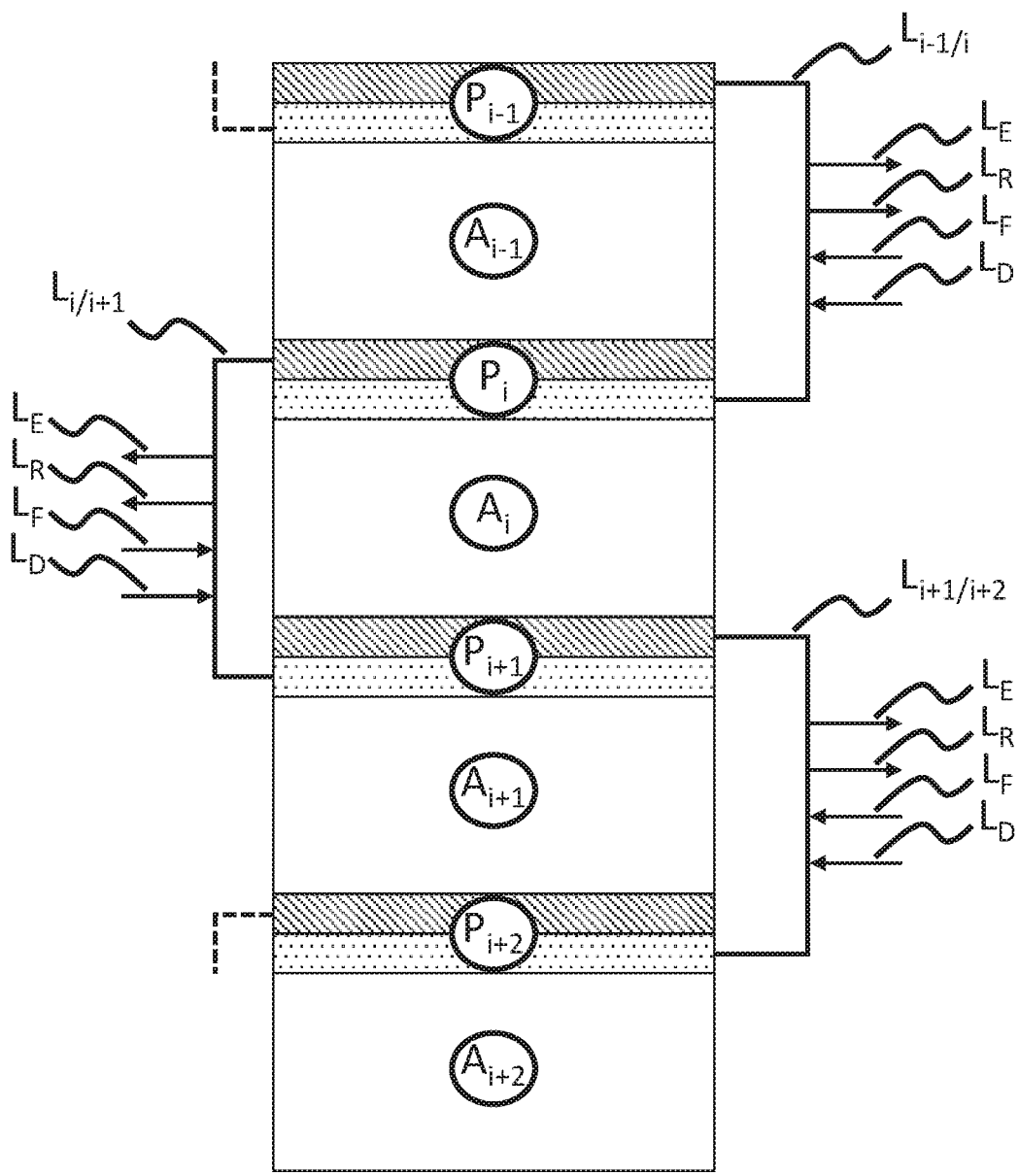

SIMULATED MOVING BED SEPARATION METHOD AND DEVICE WITH BYPASS FLUID FLOW

TECHNICAL FIELD

The invention relates to the field of the separation of natural or chemical products that are difficult to separate by distillation. Use is then made of a family of methods, and of associated devices, known by the name of simulated moving bed separation methods or devices, using either simulated countercurrent flow or simulated concurrent flow, and that will be referred to hereinafter by the abbreviation "SMB".

The fields concerned are, notably and not exclusively:

the separation of, on the one hand, normal paraffins from, on the other hand, branched paraffins, naphthenes and aromatics;

olefin/paraffin separation;

separation of paraxylene from other C8 aromatic isomers;

separation of metaxylene from other C8 aromatic isomers; and separation of ethylbenzene from other C8 aromatic isomers.

Outside of refinery and petrochemical complexes, there are numerous other applications including glucose/fructose separation, the separation of cresol position isomers, optical isomers, etc.

PRIOR ART

SMB separation is well known in the prior art. As a general rule, a column using simulated moving bed technology comprises at least three zones, and possibly four or five, each of these zones being made up of a certain number of successive beds, and each zone being defined by its position between a feed point and a withdrawal point. Typically, an SMB column is fed with at least one feedstock that is to be fractionated and with a desorbent (sometimes referred to as an eluent), and at least one raffinate and an extract are withdrawn from said column.

The feed and withdrawal points are modified over the course of time, typically shifted in the same direction by an amount corresponding to one bed.

By definition, each of the operating zones is designated by a number:

zone 1=zone for the desorption of the compounds from the extract, this zone being comprised between the injection of the desorbent and the tapping-off of the extract;

zone 2=zone for the desorption of the compounds from the raffinate, this zone being comprised between the tapping-off of the extract and the injection of the feedstock that is to be fractionated;

zone 3=zone for the adsorption of the compounds from the extract, this zone being comprised between the injection of the feedstock and the withdrawal of the raffinate; and optionally a zone 4 situated between the withdrawal of the raffinate and the injection of the desorbent.

The state-of-the-art describes in depth the various devices and methods that make it possible to achieve the separation of feedstocks in a simulated moving bed.

Particular mention may be made of patents U.S. Pat. Nos. 2,985,589, 3,214,247, 3,268,605, 3,592,612, 4,614,204, 4,378,292, 5,200,075, 5,316,821. These patents also describe in detail the operation of an SMB device.

SMB devices typically comprise at least one column (and often two), divided into a plurality of successive beds of adsorbent, said beds being separated by plates.

The controlled fluid distribution and extraction means of an SMB device typically employ one of the following two broad types of technology:

either, for each plate, a plurality of controlled on/off valves for feeding or withdrawing the fluids, these valves typically being situated in the immediate vicinity of the corresponding plate. Each plate typically comprises at least four two-way valves, controlled on an on/off basis, in order respectively to feed the feedstock and the desorbent and withdraw the extract and the raffinate;

or a multi-way rotary valve for feeding or withdrawing fluids across all of the plates.

The present invention notably falls within the context of SMB devices that employ a plurality of valves for feeding and withdrawing the various fluids.

Each of the plates typically comprises a plurality of distribution—mixing—extraction panels, referred to as "DME plates" fed by distribution/extraction lines or systems. The plates may be of any type and of any geometry. They are generally divided into panels, corresponding to adjacent sectors of the cross section of the column, for example panels with angular sectors, as disclosed in patent U.S. Pat. No. 6,537,451 FIG. 8, or panels with parallel sectors as cut from a circumference, as described in patent U.S. Pat. No. 6,797,175.

Distribution across each of the beds requires collection of the main stream coming from the previous bed, the possibility of injecting an auxiliary fluid or secondary fluid while at the same time mixing these two fluids as well as possible, or else the possibility of tapping off part of the collected fluid, extracting it in order to send it out of the device and also of redistributing a fluid across the next bed.

One generic problem with all SMB devices is that of minimizing the contamination generated by the liquid lying in the various zones of the circuit or circuits feeding fluids to and withdrawing fluids from the plates, when the feed and withdrawal points are modified during the course of operation of the SMB device.

Specifically, when, during the course of the operating sequence, a line, chamber or zone for the feeding of a plate is no longer flushed with a process fluid, it becomes a dead zone in which the liquid stagnates, and is not set back in motion again until another process fluid circulates through it again. Because of the way in which the SMB device operates, this is then a process fluid that generally differs from the fluid that has stagnated in the line concerned.

The mixing, or short-term circulation, of fluids with notably different compositions introduces disturbances into the concentration profile in the zone concerned in comparison with the ideal operation, for which discontinuities in composition are to be avoided.

Another problem lies in the potential recirculations between different zones of the one same plate, and more generally of the entire distribution/extraction system of the one same plate, as a result of very small differences in pressure between the various zones of the plate, something which still introduces disturbances in comparison with the ideal operation.

In order to address these problems associated with recirculations and dead zones, there are various techniques known in the prior art.

Flushing the distribution/extraction system of a given plate with relatively pure desorbent or desired product has already been proposed. This technique does actually make it possible to avoid the desired product being contaminated at the time of its extraction. However, because the flushing liquid has a composition that differs greatly from the liquid it is displacing, this introduces discontinuities in composition which are detrimental to the ideal operation. This first flushing variant typically performs short-term flushing with high concentration gradient. These flushing operations are short in term specifically in order to limit the effects of the discontinuities in composition.

Another solution, as described in patents U.S. Pat. Nos. 5,972,224 and 6,110,364, is to cause the majority of the main stream to pass towards the inside of the column and a minority of this stream (typically from 1% to 20% of the main stream) to pass towards the outside via external bypass lines running between successive plates. This flushing of the distribution/extraction system at the level of a plate using a stream taken from the plate above is typically performed continuously, so that the lines and zones of the distribution/extraction system are no longer "dead" but constantly flushed.

Such a system with continuous flushing via bypass lines is disclosed in FIG. 2 of patent FR 2,772,634. The bypass lines are generally small in diameter and comprise a small-diameter valve, thereby reducing the cost of the system.

According to the teaching of patents U.S. Pat. Nos. 5,972,224 and 6,110,364, the desired outcome is for the distribution/extraction system of a given plate to be flushed with liquid that has a composition very similar to that of the liquid displaced (liquid present in the distribution system, or circulating at the level of the plate). In this way, the mixing of fluids of different compositions is minimized and the discontinuities in composition are reduced.

To this end, patents U.S. Pat. Nos. 5,972,224 and 6,110,364 recommend implementing flushing flow rates in the bypasses such that the rate of passage through each bypass is substantially the same as the rate at which the concentration gradient in the main stream of the SMB device advances. The flushing is then said to be "synchronous" or "at synchronous flow rate". Thus, the various lines and volumes are flushed with a fluid that has a composition substantially identical to that of the liquid found therein, and the liquid circulating through a bypass is reintroduced at a point at which the composition of the main stream is substantially identical.

The flushing operations are therefore synchronous, long in duration and performed at a low or zero concentration gradient. According to the teaching of the prior art, flushing is said to be "synchronous" when the flushing flow coming from one plate towards the next plate is equal to V/ST in which V is the cumulative volume of the distribution systems of the said plates, and of the volume of the bypass line extending between these two plates and ST is the changeover period of the SMB device (the period between two successive feed/extraction changeovers).

Thus:

"synchronous flow rate"=$QS_{i/i+1}=(V_i+V_{i+1}+VL_{i/i+1})/ST$, where:

$QS_{i/i+1}$ denotes the flow rate of the flushing flow coming from plate $P_i$ towards the next plate (typically the plate below) $P_{i+1}$;

$V_i$ denotes the volume of the distribution/extraction system of the starting plate $P_i$;

$V_{i+1}$ denotes the volume of the distribution/extraction system of the destination plate $P_{i+1}$;

$VL_{i/i+1}$ denotes the volume of the bypass line extending between $P_i$ and $P_{i+1}$; and ST denotes the changeover period.

Synchronous flushing is typically implemented using flushing at a controlled flow rate, adapted to suit each of the zones, ranging from 50% to 150% of the synchronous flow rate in these zones, and ideally representing 100% of the synchronous flow rate. The flow rates in the bypass lines of the 4 zones of the SMB device are controlled by regulating means in each bypass line.

Patent FR 2,935,100 shows that it is possible to improve the performance of the method by regulating the flow rates in the bypass lines in a given operating zone according to whether or not at least one closed bypass line is present in said zone. More specifically, the oversynchronism of the non-closed bypass lines of a zone in which there is at least one closed bypass line is defined as the ratio of the number of closed bypass lines in the zone concerned to the total number of bypass lines in that zone, namely to the number of beds in the zone concerned.

The oversynchronism S is defined by the following formula:

$$S=a+b(nf/nt)$$

in which:

a is a constant comprised between −5 and 5, b is a constant comprised between 40 and 100, of denotes the number of closed bypass lines in the zone concerned, and nt denotes the total number of bypass lines in the zone concerned.

Patent FR 2,935,100 also teaches that it is necessary to close one bypass line for each stream (feedstock and desorbent) injected and for each stream (extract and raffinate) withdrawn.

The above mentioned methods make it possible to obtain the objective of commercial purity. However, the Applicant Company has been able to demonstrate that, while the "synchronous flushing" teachings of patents U.S. Pat. Nos. 5,972,224, 6,110,364 and FR 2,935,100 afford an improvement over the prior art, it was, surprisingly, still possible to improve the operation and performance of simulated moving bed separation methods still further.

SUMMARY

In the context described hereinabove, a first object of the present description is to provide a simulated moving bed separation method that makes it possible, for the same purity, to extract a solute from the feedstock with higher yield, notably by providing a leakage flow on the bypass lines via which a stream is injected or withdrawn. A second object is to provide a method that makes it possible, for equivalent yield, to extract a solute from the feedstock with a higher purity.

According to a first aspect, the aforementioned objects, together with other advantages, are obtained by a method for the simulated moving bed separation of a feedstock in a simulated moving bed separation device, the device comprising:

at least one column comprising a plurality of beds of adsorbent which are separated by plates each comprising a distribution/extraction system; and external bypass lines directly joining two successive plates, each external bypass line comprising fluid feed points and effluent withdrawal points, in which method:

the at least one column is fed with the feedstock and a desorbent and at least one extract and at least one raffinate is withdrawn from the at least one column, the feed and withdrawal points being shifted during the course of time by an amount corresponding to one adsorbent bed with a changeover period and determining a plurality of operating zones of the device, and notably the following main zones:

a zone 1 for the desorption of the compounds from the extract, this zone being comprised between the feed for the desorbent and the withdrawal of the extract, a zone 2 for the desorption of the compounds from the raffinate, this zone being comprised between the withdrawal of the extract and the feed for the feedstock, a zone 3 for the adsorption of the compounds from the extract, this zone being comprised between the feed for the feedstock and the withdrawal of the raffinate, and a zone 4 situated between the withdrawal of the raffinate and the feed for the desorbent;

when a fluid is injected towards a chosen plate via an external bypass line connected to the said chosen plate, the flow rate within the said external bypass line is controlled in such a way that a major proportion of the fluid is injected towards the chosen plate, and that a minor proportion of the fluid is injected towards the adjacent plate connected to the said external bypass line; and/or When an effluent is withdrawn from a chosen plate via an external bypass line connected to the said chosen plate, the flow rate within the said external bypass line is controlled in such a way that a major proportion of the effluent is withdrawn from the chosen plate, and that a minor proportion of the effluent is withdrawn from the adjacent plate connected to the said external bypass line.

According to one or more embodiments, the minor proportion of the fluid injected towards the adjacent plate connected to the said external bypass line is regulated in such a way that a level of rinsing of the said adjacent plate is equal to 100%+/−30%; and/or the minor proportion of the effluent withdrawn from the adjacent plate connected to the said external bypass line is regulated in such a way that a level of rinsing of the said adjacent plate is equal to 100% +/−30%, the adjacent plate being the upstream adjacent plate positioned upstream of the chosen plate, or the downstream adjacent plate positioned downstream of the chosen plate, the level of rinsing of the upstream adjacent plate being defined by $Q_{i-1} \times ST/(V_{i-1}+VL_{i-1/i}/2)$, the level of rinsing of the downstream adjacent plate being defined by $Q_{i+1} \times ST/(V_{i+1}+VL_{i/i+1}/)$, n being the number of adsorbent beds in the column, i being a natural whole number comprised between 1 and n, $Q_{i-1}$ denoting the volumetric flow rate flowing from the upstream adjacent plate, $Q_{i+1}$ denoting the volumetric flow rate flowing towards the downstream adjacent plate, $V_{i-1}$ denoting the volume of the distribution/extraction system of the upstream adjacent plate, $V_{i+1}$ denoting the volume of the distribution/extraction system of the downstream adjacent plate, $VL_{i-1/i}$ denoting the volume of the upstream external bypass line between the upstream adjacent plate and the chosen plate, $VL_{i/i+1}$ denoting the volume of the downstream external bypass line between the downstream adjacent plate and the chosen plate, ST denoting the changeover period.

According to one or more embodiments, the minor proportion of the fluid injected towards the adjacent plate connected to the said external bypass line is regulated in such a way that a level of rinsing of the said adjacent plate is equal to 100% +/−20%; and/or the minor proportion of the effluent withdrawn from the adjacent plate connected to the said external bypass line is regulated in such a way that a level of rinsing of the said adjacent plate is equal to 100% +/−20%.

According to one or more embodiments, synchronism to within plus or minus 10% is established in each other external bypass line, the synchronism flow rate being defined by $(V_j+V_{j+1}+VL_{j/j+1})/ST$, j being a natural whole number comprised between 1 and n and different from i, n being the number of adsorbent beds in the column, i being a natural whole number comprised between 1 and n;

$V_j$ and $V_{j+1}$ denoting the respective volumes of the distribution/extraction systems of the plates connected to the said other external bypass line, $VL_{j/j+1}$ denoting the volume of the said other external bypass line, ST denoting the changeover period.

According to one or more embodiments, synchronism to within plus or minus 5% is established in each other external bypass line.

According to one or more embodiments, n is a natural whole number comprised between 6 and 24, and preferably between 8 and 15.

According to one or more embodiments, each plate is connected to an upstream external bypass line between the upstream adjacent plate and the said plate, and to a downstream external bypass line between the said plate and the downstream adjacent plate.

According to one or more embodiments, each plate comprises a plurality of distribution—mixing—extraction panels of the parallel sectors type with asymmetric feed.

According to one or more embodiments, the feedstock contains paraxylene or metaxylene within a mixture of C8 aromatic hydrocarbons.

Embodiments according to the first aspect, together with other features and advantages of the methods according to the first aspect, will become apparent on reading the description which will follow, given solely by way of illustration and without limitation, and with reference to the following drawings.

BRIEF DESCRIPTION OF THE DRAWINGS

FIG. 1 depicts an SMB device used in the method according to embodiments of the present description, the device comprising a column having a succession of plates ($P_{i-1}, P_i, P_{i+1}, P_{i+2}$) and of beds ($A_{i-31\ 1}, A_i, A_{i+1}, A_{i+2}$), and external bypass lines ($L_{i-1/i}, L_{i/i+1}, L_{i+1/i+2}$).

DETAILED DESCRIPTION

The object of the invention is to improve the performance of a simulated bed separation device in comparison with the teachings of patents U.S. Pat. Nos. 5,972,224, 6,110,364 and FR 2,935,100.

With reference to FIG. 1, in order to improve the separation performance achievable using SMB technology, the invention proposes a method for the SMB separation of a feedstock F in an SMB device possessing at least one column, said column being made up of a plurality of beds of adsorbent $A_i$, separated by plates $P_i$ each comprising a distribution/extraction system. The SMB device further comprises external bypass lines $L_{i/i+1}$ directly joining two successive plates $P_i$, $P_{i+1}$, notably allowing said plates to be flushed. It being possible for each of these bypass lines $L_{i/i+1}$ to comprise automated means for regulating the flushing flow rate.

According to one or more embodiments, the column comprises n adsorbent beds $A_i$. According to one or more embodiments, n is a natural whole number comprised between 6 and 24, preferably between 8 and 15, i being a natural whole number comprised between 1 and n.

The SMB separation method comprises the following steps: the feedstock F and a desorbent D are fed, and at least one extract E and at least one raffinate R are withdrawn, the feed and withdrawal points being shifted over the course of time by an amount corresponding to one adsorbent bed, with a changeover period (denoted ST) and determining a plurality of operating zones of the SMB device, and notably the following main zones:

a zone 1 for the desorption of the compounds from the extract, this zone being comprised between the feed for the desorbent D and the withdrawal of the extract E;

a zone 2 for the desorption of the compounds from the raffinate, this zone being comprised between the withdrawal of the extract E and the feed for the feedstock F;

a zone 3 for the adsorption of the compounds from the extract, this zone being comprised between the feed for the feedstock and the withdrawal of the raffinate R; and a zone 4 situated between the withdrawal of the raffinate R and the feed for the desorbent D.

It should be noted that an external bypass line $L_{i/i+1}$ directly joining two successive plates $P_i$, $P_{i+1}$, is said to belong to a zone when the bed $A_i$ situated between the plates $P_i$ and $P_{i+1}$ belongs to said zone. In addition, the n adsorbent beds $A_i$ are distributed between zones 1 to 4 in configurations referred to as being of type a/b/c/d, which means to say that the distribution of the beds is as follows:

a is the number of beds in zone 1;
b is the number of beds in zone 2;
c is the number of beds in zone 3; and
d is the number of beds in zone 4.

According to one or more embodiments:
a=(n*0.208)*(1±0.2);
b=(n*0.375)*(1±0.2);
c=(n*0.292)*(1±0.2);
d=(n*0.125)*(1±0.2).

Patent FR 2,935,100 teaches that it is necessary to close one bypass line for each stream (feedstock and desorbent) injected and for each stream (extract and raffinate) withdrawn.

By contrast, in the method according to the invention, the bypass lines are kept open and the leakage flow rate thus generated is controlled.

More specifically, when a fluid (feedstock S or desorbent D) is injected into a chosen plate $P_i$, use is made of an injection line $L_F$ or $L_D$. This line is connected to a bypass line connected to the said plate, namely either to the bypass line $L_{i-1/i}$, or to the bypass line $L_{i/i+1}$. The "adjacent plate connected to the said bypass line" is referred to as the plate $P_{i-1}$ if the bypass line concerned is the line $L_{i-1/i}$, or the plate $P_{i+1}$ if the bypass line concerned is the line $L_{i/i+1}$. Whatever the bypass line connected to the injection line used, the flow rate within the said line is controlled in such a way that the majority of the injected stream flows towards the chosen plate $P_i$, and a (non-zero) proportion of the injected stream flows to the adjacent plate connected to the said bypass line (e.g. from 1% to 20% of the stream).

According to one or more embodiments, the minor proportion of the stream flowing towards the adjacent plate connected to the said bypass line is regulated in such a way as to ensure a level of rinsing of the adjacent plate connected to the said bypass line equal to 100% +/−30%, preferably equal to 100% +/−20%, and for preference equal to 100% +/−10%.

Likewise, when an effluent (extract E or raffinate R) is withdrawn from a chosen plate $P_i$, use is made of a withdrawal line $L_E$ or $L_R$. This withdrawal line is connected to a bypass line connected to the said plate, namely either to the bypass line $L_{i-1/i}$, or to the bypass line $L_{i/i+1}$ The "adjacent plate connected to the said bypass line" is referred to as the plate $P_{i-1}$ if the bypass line concerned is the line $L_{i-1/i}$, or the plate $P_{i+1}$ if the bypass line concerned is the line $L_{i/i+1}$. Whatever the bypass line connected to the withdrawal line used, the flow rate within the said line is controlled in such a way that the majority of the withdrawn stream flows from the chosen plate $P_i$, and a (non-zero) proportion of the withdrawn stream flows from the adjacent plate connected to the said bypass line.

According to one or more embodiments, the minor proportion of the stream flowing from the adjacent plate connected to the said bypass line is regulated in such a way as to ensure a level of rinsing of the adjacent plate connected to the said bypass line equal to 100% +/−20%.

With the plate adjacent to the chosen plate $P_i$ being either the upstream adjacent plate ($P_{i-1}$) positioned upstream of the chosen plate ($P_i$), or the downstream adjacent plate ($P_{i+1}$) positioned downstream of the chosen plate ($P_i$), the level of rinsing of the plate $P_{i-1}$ is defined as $Q_{i-1} \times ST/(V_{i-1}+VL_{i-1/i}/2)$ and the level of rinsing of the plate $P_{i+1}$ as $Q_{i+1} \times ST/(V_{i+1}+VL_{i/i+1}/2)$. In these expressions:

$Q_{i-1}$ denotes the volumetric flow rate flowing from the plate $P_{i-1}$;

$Q_{i+1}$ denotes the volumetric flow rate flowing towards the plate $P_{i+1}$;

$V_{i-1}$ denotes the volume of the distribution/extraction system of the upstream adjacent plate $P_{i-1}$;

$V_{i+1}$ denotes the volume of the distribution/extraction system of the downstream adjacent plate $P_{i+1}$;

$VL_{i/i+1}$ denotes the volume of the bypass line extending between $P_i$ and $P_{i+1}$;

$VL_{i-1/i}$ denotes the volume of the bypass line extending between $P_{i-1}$ and $P_i$; and ST denotes the changeover period.

There is established in all the other bypass lines of the method according to the invention (i.e. the bypass lines into which a fluid (e.g. feedstock or desorbent) is not being injected or an effluent (e.g. extract or raffinate) is not being withdrawn) a flow rate corresponding to synchronism, to within plus or minus 10%, and preferably to within plus or minus 5%, the synchronism flow rate being defined by $(V_j+V_{j+1}+VL_{j/j+1})/ST$, in which expression:

j is a natural whole number comprised between 1 and n and different from i;

$V_j$ and $V_{j+1}$ denote the respective volumes of the distribution/extraction systems of the plates ($P_j$ and $P_{j+1}$) connected to the said other external bypass line ($L_j/L_{j+1}$);

$VL_{j/j+1}$ denotes the volume of the bypass line extending between $P_j$ and $P_{j+1}$; and ST denotes the changeover period.

Each plate $P_i$ comprises two chambers for accomplishing the sequential operations of feeding the feedstock F or injecting the desorbent D and extracting the raffinate R or the extract E. The present invention relates to columns having two chambers per plate $P_i$. There are a number of possible solutions for using the two chambers, each one of them being able to be used for the injection or the withdrawal of one or more streams. For example, a first chamber may perform the operations of injecting feedstock F or desorbent D, and the other chamber performs the operations of withdrawing raffinate R or extract E. Another possible scenario is to use one chamber for injecting the feedstock F and withdrawing the raffinate R, the other handling the injection of desorbent D and the withdrawal of the extract E. These two examples are nonlimiting, other uses of the two chambers being possible. Each bed i is equipped with a bypass line which connects one chamber of the upstream plate to one chamber of the downstream plate.

According to one or more embodiments, the feedstock is selected from the group consisting of a mixture of essentially C8 aromatic compounds (e.g. xylenes and ethylbenzene). According to one or more embodiments, the mixture comprises at least 95%, preferably at least 97% (e.g. at least 99%) of essentially C8 aromatic compounds.

The method according to the present invention more particularly applies to the separation of a feedstock containing paraxylene or metaxylene within a mixture of C8 aromatic hydrocarbons. According to one or more embodiments, the feedstock comprises at least 15 wt % of paraxylene and/or 30 wt % [to be completed] of metaxylene with respect to the total weight of the feedstock.

One example of an SMB separation method of great industrial importance is the separation of C8 aromatic fractions in order to produce paraxylene of commercial purity, typically at a purity of at least 99.7 wt %, and a raffinate rich in ethylbenzene, orthoxylene and metaxylene.

According to one or more embodiments, the adsorbent is selected from the group made up of zeolites of the faujasite type, of type NaY, BaX, BaKX, BaLSX. For preference, the adsorbent is selected from the group made up of BaX, BaKX, NaY.

According to one or more embodiments, the desorbent is selected from the group made up of one or more isomers of diethylbenzene and toluene. For preference, the desorbent is selected from the group made up of paradiethylbenzene and toluene.

According to one or more embodiments, the temperature of the column is comprised between 120° C. and 190° C. For preference, the temperature of the column is comprised between 150° C. and 180° C.

According to one or more embodiments, the pressure in the column is comprised between 0.3 MPa and 3 MPa. According to one or more embodiments, the pressure in the column is comprised between 0.5 MPa and 3 MPa. According to one or more embodiments, the pressure in the column is comprised between 0.8 MPa and 3 MPa. For preference, the pressure in the column is comprised between 1 MPa and 2 MPa.

According to one or more embodiments, the changeover period ST used is comprised between 20 seconds and 120 seconds. For preference, the changeover period ST used is comprised between 40 seconds and 100 seconds.

Of course, these application examples are entirely non-limiting, and other applications are possible, notably in the field of the separation of normal and iso paraffins or normal and iso olefins.

EXAMPLES

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 18/55.449, filed Jun. 20, 2018, are incorporated by reference herein.

The invention will be better understood from reading the following examples.

Example 1 (Reference Method)

Consider an SMB unit made up of 15 beds, of length 1.3 m and of internal radius 3.5 m, with a feedstock injection line $L_F$, a desorbent (which may also be referred to as eluent or solvent) injection line $L_D$, an extract withdrawal line $L_E$ and a raffinate withdrawal line $L_R$ is considered. The plates have two mixing chambers, one being an injection tank (feedstock F and desorbent D), the other being a withdrawal tank (extract E and raffinate R). The total volume ($V_i + V_{i+1} + VL_{i/i+1}$), $VL_{i/i+1}$ where is the volume of the bypass line from plate $P_i$ to plate $P_{i+1}$ and where $V_i$ is the volume of the distribution/extraction system for plate $P_i$, represents 3% of the volume of the bed comprised between plate $P_i$ and plate $P_{i+1}$.

The effluent withdrawal lines ($L_R$ for the raffinate R and $L_E$ for the extract E) are situated downstream of a bypass line isolation valve (referred to more simply as "downstream of the bypass line valve"). The injection lines ($L_F$ for the feedstock F and $L_D$ for the desorbent D) are situated upstream of the isolation valve.

When a fluid (feedstock F or desorbent D) is injected at plate $P_i$, use is made of an injection line connected to the bypass line $L_{i/i+1}$. According to the reference method, the isolation valve isolating the bypass line $L_{i/i+1}$ is closed to ensure that the injected fluid does indeed flow towards the plate $P_i$.

When an effluent (extract E or raffinate R) is withdrawn at plate $P_i$, use is made of a withdrawal line connected to the bypass line $L_{i-1/i}$. According to the reference method, the isolation valve isolating the bypass line $L_{i-1/i}$ is closed to ensure that the injected fluid does indeed flow towards the plate $P_i$.

The result of this is that use of this type of bypass line notably leads to:

closure of two bypass lines in zone 1 (injection of the desorbent via a line connected to the bypass line bypassing the first bed in zone 1, and withdrawal of the extract via a line connected to a bypass line bypassing the final bed in zone 1); and closure of two bypass lines in zone 3 (injection of the feedstock via a line connected to the bypass line bypassing the first bed in zone 3, and withdrawal of the raffinate via a line connected to a bypass line bypassing the final bed in zone 3).

The beds are distributed in the 3/6/4/2 configuration, which means to say that the distribution of the beds is as follows:

3 beds in zone 1;
6 beds in zone 2;
4 beds in zone 3; and
2 beds in zone 4.

The adsorbent used is a zeolite of type BaX, and the desorbent is paradiethylbenzene. The temperature of the column is 175° C., and the pressure is 1.5 MPa.

The feedstock is made up of 23 wt % of paraxylene, of 22 wt % of orthoxylene, of 50 wt % of metaxylene, and of 5 wt % of ethylbenzene with respect to the total weight of the feedstock.

The changeover period ST employed is 45 seconds.

The feedstock and desorbent injection liquid flow rates are as follows:

816 m$^3$.h$^{-1}$ for the feedstock; and
1026 m$^3$.h$^{-1}$ for the desorbent,
namely a solvent ratio S/F=1.3.

The synchronism is set at 100% for all the open bypass lines.

By simulation, a paraxylene purity of 99.76% and a paraxylene yield of 96.27% are obtained.

Example 2 (Method According to the Invention)

Consider an SMB unit made up of 15 beds, of length 1.3 m and of internal radius 3.5 m, with a feedstock injection line $L_F$, a desorbent (which may also be referred to as eluent or solvent) injection line $L_D$, an extract withdrawal line $L_E$ and a raffinate withdrawal line $L_R$ is considered. The plates have two mixing chambers, one being an injection tank (feedstock F and desorbent D), the other being a withdrawal tank (extract E and raffinate R).

The total volume $(V_i+V_{i+1}+VL_{i/i+1})$, where $VL_{i/i+1}$ is the volume of the bypass line from plate $P_i$ to plate $P_{i+1}$ and where $V_i$ is the volume of the distribution/extraction system for plate $P_i$, represents 3% of the volume of the bed comprised between plate $P_i$ and plate $P_{i+1}$.

The effluent withdrawal lines ($L_R$ for the raffinate R and $L_E$ for the extract E) are situated downstream of a bypass line isolation valve (referred to more simply as "downstream of the bypass line valve"). The injection lines ($L_F$ for the feedstock F and $L_D$ for the desorbent D) are situated upstream of the isolation valve.

When a fluid (feedstock F or desorbent D) is injected at plate $P_i$, use is made of an injection line connected to the bypass line $L_{i/i+1}$. According to the method according to the invention, the injected fluid flows predominantly towards the plate $P_i$ and a minor proportion of the injected fluid flows within the bypass line $L_{i/i+1}$ towards the plate $P_{i+1}$. This minor proportion is regulated in such a way as to ensure a level of rinsing of 100% for the plate $P_{i+1}$.

When an effluent (extract E or raffinate R) is withdrawn at plate $P_i$, use is made of a withdrawal line connected to the bypass line $L_{i-1/i}$. According to the method according to the invention, the withdrawn fluid comes predominantly from the plate $P_i$, and a minor proportion of the withdrawn fluid comes from the plate $P_{i-1}$. This minor proportion is regulated in such a way as to ensure a level of rinsing of 100% for the plate $P_{i-1}$.

The beds are distributed in the 3/6/4/2 configuration, which means to say that the distribution of the beds is as follows:

3 beds in zone 1;
6 beds in zone 2;
4 beds in zone 3; and
2 beds in zone 4.

The adsorbent used is a zeolite of type BaX, and the desorbent is paradiethylbenzene. The temperature of the column is 175° C., and the pressure is 1.5 MPa.

The feedstock is made up of 23 wt % of paraxylene, of 22 wt % of orthoxylene, of 50 wt % of metaxylene, and of 5 wt % of ethylbenzene with respect to the total weight of the feedstock.

The changeover period ST employed is 45 seconds.

The feedstock and desorbent injection liquid flow rates are as follows:

816 m$^3$.h$^{-1}$ for the feedstock; and
1026 m$^3$.h$^{-1}$ for the desorbent,
namely a solvent ratio S/F=1.3.

The synchronism is set at 100% for all the open bypass lines.

By simulation, a paraxylene purity of 99.78% and a paraxylene yield of 97.16% are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Method for the simulated moving bed separation of a feedstock (F) in a simulated moving bed separation device, the device comprising:
at least one column comprising a plurality of beds of adsorbent ($A_i$) which are separated by plates ($P_i$) each comprising a distribution/extraction system; and
external bypass lines ($L_{i/i+1}$) directly joining two successive plates ($P_i$, $P_{i+1}$), each external bypass line comprising fluid (F, D) feed points and effluent (E, R) withdrawal points,
in which method:
the at least one column is fed with the feedstock (F) and a desorbent (D) and at least one extract (E) and at least one raffinate (R) is withdrawn from the at least one column, the feed and withdrawal points being shifted during the course of time by an amount corresponding to one adsorbent bed with a changeover period (ST) and determining a plurality of operating zones of the device, and notably the following main zones:
a zone 1 for the desorption of the compounds from the extract, this zone being comprised between the feed for the desorbent (D) and the withdrawal of the extract (E),
a zone 2 for the desorption of the compounds from the raffinate, this zone being comprised between the withdrawal of the extract (E) and the feed for the feedstock (F),
a zone 3 for the adsorption of the compounds from the extract, this zone being comprised between the feed for the feedstock (F) and the withdrawal of the raffinate (R), and
a zone 4 situated between the withdrawal of the raffinate (R) and the feed for the desorbent (D);
when a fluid (F, D) is injected towards a chosen plate ($P_i$) via an external bypass line ($L_{i-1/i}$, $L_{i/i+1}$) connected to the said chosen plate ($P_i$), the flow rate within the said external bypass line ($L_{i-1/i}$, $L_{i/i+1}$) is controlled in such a way that a major proportion of the fluid (F, D) is injected towards the chosen plate ($P_i$), and that a minor proportion of the fluid (F, D) is injected towards the adjacent plate ($P_{i-1}$, $P_{i+1}$) connected to the said external bypass line ($L_{i-1/i}$, $L_{i/i+1}$); and/or
when an effluent (E, R) is withdrawn from a chosen plate ($P_i$) via an external bypass line ($L_{i-1/i}$, $L_{i/i+1}$) connected to the said chosen plate ($P_i$), the flow rate within the said external bypass line ($L_{i-1/i}$, $L_{i/i+1}$) is controlled in such a way that a major proportion of the effluent (E, R) is withdrawn from the chosen plate ($P_i$), and that a minor proportion of the effluent (E, R) is withdrawn from the adjacent plate ($P_{i-1}$, $P_{i+1}$) connected to the said external bypass line ($L_{i-1/i}$, $L_{i/i+1}$).

2. Method according to claim 1, in which:
the minor proportion of the fluid (F, D) injected towards the adjacent plate ($P_{i-1}$, $P_{i+1}$) connected to the said external bypass line ($L_{i-1/i}$, $L_{i/i+1}$) is regulated in such a way that a level of rinsing of the said adjacent plate ($P_{i-1}$, $P_{i+1}$) is equal to 100% +/−30%; and/or
the minor proportion of the effluent (E, R) withdrawn from the adjacent plate ($P_{i-1}$, $P_{i+1}$) connected to the said external bypass line ($L_{i+1/i}$, $L_{i/i+1}$) is regulated in such a way that a level of rinsing of the said adjacent plate ($P_{i-1}$, $P_{i+1}$) is equal to 100% +/−30%,
the adjacent plate ($P_{i-1}$, $P_{i+1}$) being the upstream adjacent plate ($P_{i-1}$) positioned upstream of the chosen plate ($P_i$), or the downstream adjacent plate ($P_{i+1}$) positioned downstream of the chosen plate ($P_i$),
the level of rinsing of the upstream adjacent plate ($P_{i-1}$) being defined by $Q_{i-1} \times ST/(V_{i-1}+VL_{i-1/i}/2)$
the level of rinsing of the downstream adjacent plate ($P_{i-1}$) being defined by $Q_{i+1}i \times ST/(V_{i+1}+VL_{i/i+1}/2)$,
n being the number of adsorbent beds in the column,
i being a natural whole number comprised between 1 and n,
$Q_{i-1}$ denoting the volumetric flow rate flowing from the upstream adjacent plate ($P_{i-1}$),
$Q_{i+1}$ denoting the volumetric flow rate flowing towards the downstream adjacent plate ($P_{i-1}$);
$V_{i-1}$ denoting the volume of the distribution/extraction system of the upstream adjacent plate ($P_{i-1}$);
$V_{i+1}$ denoting the volume of the distribution/extraction system of the downstream adjacent plate ($P_{i+1}$);
$VL_{i-1/i}$ denoting the volume of the upstream external bypass line ($L_{i-1/i}$) between the upstream adjacent plate ($P_{i-1}$) and the chosen plate ($P_i$),
$VL_{i/i+1}$ denoting the volume of the downstream external bypass line ($L_{i/i+1}$) between the chosen plate ($P_i$) and the downstream adjacent plate ($P_{i+1}$),
ST denoting the changeover period.

3. Method according to claim 2, in which:
the minor proportion of the fluid (F, D) injected towards the adjacent plate ($P_{i-1}$, $P_{i+1}$) connected to the said external bypass line ($L_{i-1/i}$, $L_{i/i+1}$) is regulated in such a way that a level of rinsing of the said adjacent plate ($P_{i-1}$, $P_{i+1}$) is equal to 100% +/−20%; and/or
the minor proportion of the effluent (E, R) withdrawn from the adjacent plate ($P_{i-1}$, $P_{i+1}$) connected to the said external bypass line $L_{i+1}/i$, $L_{i/i+1}$) is regulated in such a way that a level of rinsing of the said adjacent plate ($P_{i-1}$, $P_{i+1}$) is equal to 100% +/−20%.

4. Method according to claim 1, in which:
synchronism to within plus or minus 10% is established in each other external bypass line ($L_j/L_{j+1}$),
the synchronism flow rate being defined by $(V_j+V_{j+1}+V_{j/j+1})/ST$,
j being a natural whole number comprised between 1 and n and different from i,
n being the number of adsorbent beds in the column,
i being a natural whole number comprised between 1 and n,
$V_j$ and $V_{j+1}$ denoting the respective volumes of the distribution/extraction systems of the plates ($P_j$ and $P_{j+1}$) connected to the said other external bypass line ($L_j/L_{j+1}$),
$VL_{j/j+1}$ denoting the volume of the said other external bypass line ($L_j/L_{j+1}$),
ST denoting the changeover period.

5. Method according to claim 4, in which synchronism to within plus or minus 5% is established in each other external bypass line ($L_j/L_{j+1}$).

6. Method according to claim 2, in which n is a natural whole number comprised between 6 and 24.

7. Method according to claim 1, in which each plate ($P_i$) is connected to an upstream external bypass line ($L_{i+1/i}$) between the upstream adjacent plate ($P_{i+1}$) and the said plate ($P_i$), and/or to a downstream external bypass line ($L_{i/i+1}$) between the said plate ($P_i$) and the downstream adjacent plate ($P_{i+1}$).

8. Method according to claim 1, in which each plate ($P_i$) comprises a plurality of distribution—mixing—extraction panels of the parallel sectors type with asymmetric feed.

9. Method according to claim 1, in which the feedstock (F) contains paraxylene or metaxylene within a mixture of C8 aromatic hydrocarbons.

* * * * *